US00PP08391P

United States Patent [19]

Meilland

[11] Patent Number: Plant 8,391

[45] Date of Patent: Sep. 28, 1993

[54] ROSE PLANT—MEIZELI VARIETY

[75] Inventor: Alain A. Meilland, Antibes, France

[73] Assignee: The Conard-Pyle Company, West Grove, Pa.

[21] Appl. No.: 921,091

[22] Filed: Jul. 29, 1992

[51] Int. Cl.[5] ..... A01H 5/00

[52] U.S. Cl. ..... Plt./18

[58] Field of Search ..... Plt./11, 18, 19

*Primary Examiner*—Howard J. Locker

*Attorney, Agent, or Firm*—Burns, Doane, Swecker & Mathis

[57] ABSTRACT

A new and distinct variety of Hybrid Tea rose plant is provided which abundantly and continuously forms attractive semi-double long lasting pink blossoms. The blossoms are Amaranth Pink on the supper surface and light amaranth pink on the under surface. The blossoms possess a very strong fragrance and the petals tend to drop cleanly. The floral buds exhibit a very elegant exhibition-type configuration. The plant exhibits a semi-erect growth habit, forms lettuce green adult wood, forms vigorous vegetation which is very decorative, and is well suited for service as attractive ornamentation in parks and gardens. Additionally, the plant is not particularly affected by cryptogamic diseases.

1 Drawing Sheet

SUMMARY OF THE INVENTION

The new variety of Hybrid Tea rose plant was created by artificial pollination wherein two parents were crossed which previously has been studied in the hope that they would contribute the desired characteristics. The female parent (i.e., the seed parent) was the product of the pollination of the Meirisouru variety (nonpatented in the United States) by the Meicesar variety (nonpatented in the United States). The male parent (e.i., the pollen parent) was the First Prize variety (U.S. Plant Pat. No. 2,774). The parentage of the new variety can be summarized as follows:

(Meirisouru × Meicesar) × First Prize.

The seeds resulting from the above pollination were sown and 112 small plants were obtained which were physically and biologically different from each other. Selective study resulted in the identification of a single plant of the new variety.

It was found that the new variety of Hybrid Tea rose plant of the present invention possesses the following combination of characteristics:

(a) forms in abundance on a continuous basis attractive long lasting semi-double pink blossoms which are Amaranth Pink on the upper surface and light Amaranth Pink on the under surface,
(b) forms floral buds which exhibit an elegant exhibition-type configuration,
(c) forms blossoms which are very fragrant,
(d) forms very decorative vigorous vegetation,
(e) exhibits a semi-erect growth habit,
(f) is particularly suited for growing in parks and gardens, and
(g) is not particularly affected by cryptogamic diseases.

The new variety well meets the needs of the horticultural industry and is particularly well suited for use as attractive ornamentation in the landscape.

The new variety has been found to undergo asexual propagation by a number of routes, including budding, grafting, cuttage, etc. Asexual propagation by the above-mentioned methods as performed in France has shown that the characteristics of the new variety are strictly transmissible from one generation to another.

The new variety has been named the Meizeli variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during September while budded on *Rosa froebelli* understock and growing outdoors at LeCannet-des-Maures, Var, France.

DETAILED DESCRIPTION

Figures 1, 2, 3, 4, 5, 6, 7, 8, 9, 10, 11, 12, 13, 14, 15, 16:
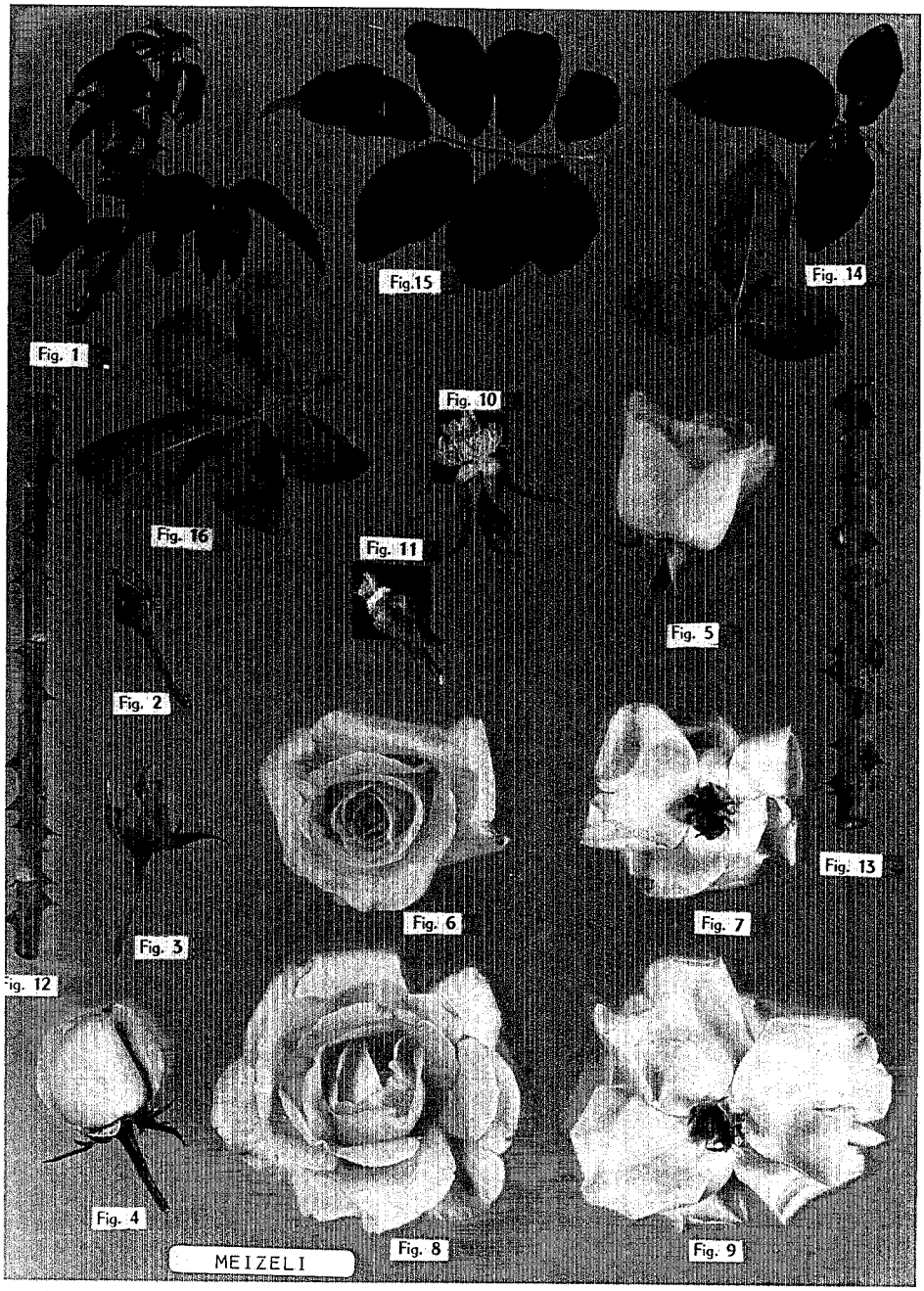
FIG. 1 illustrates a specimen of a young shoot.
FIG. 2 illustrates a specimen of a floral bud before the opening of the sepals.
FIG. 3 illustrates a specimen of a floral bud at the opening of the sepals.
FIG. 4 illustrates a specimen of a floral bud at the opening of the petals.
FIG. 5 illustrates a specimen of a flower in the course of opening.
FIG. 6 illustrates a specimen of an open flower — plan view — obverse.
FIG. 7 illustrates a specimen of an open flower — plan view — reverse.
FIG. 8 illustrates a specimen of a fully open flower — plan view — obverse.
FIG. 9 illustrates a specimen of a fully open flower — plan view — reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a segment of a flowering stem.
FIG. 13 illustrates a specimen of a segment of a main branch.
FIG. 14 illustrates specimens of leaves with three leaflets — plan view — upper surface (top and lower surface (bottom)
FIG. 15 illustrates a specimen of a leaf with seven leaflets — plan view — upper surface.
FIG. 16 illustrates a specimen of a leaf with five leaflets — plan view — under surface.

The chart used in the identification of the colors is that of The Royal Horticultural Society (R.H.S. Colour Chart). The description is based on the observation of two year old plants made during September while budded on *Rosa froebelli* understock and growing in outdoors at LeCannet-des-Maures, Var, France. The coloration in common terms precedes reference to the chart.

Class: Hybrid Tea.

Plant:

*height.*—Approximately 100 to 110 cm. on average

*Habit.*—Semi-erect.

Branches:

*Color.*—Young stems: reddish brown. Adult wood: lettuce green, Yellow-Green Group 144A.

*Throns.*—Size: medium. Quantity: numerous. Color: reddish on young stems and brownish on mature wood.

Leaves:

*Stipules.*—Adnate, pectinate, wide and linear.

*Petioles.*—Upper surface: striped reddish brown on young foliage and medium green on mature foliage with more or less glandular edges. Under surface: smooth and medium green.

*Leaflets.*—Number 3, 5, and 7. Shape: oval to elliptic. Serration: simple and regular. Texture: consistent. General appearance: dense, semi-matte foliage. Color (young foliage): Upper surface: bronze green, Yellow-Green Group 146A. Under surface: light green, Yellow-Green Group 146D. Color (adult foliage): Upper surface: medium green, Green Group 137A. Under surface: light green, Yellow-Green Group 146D.

Inflorescence:

*Number of flowers.*—Usually one single bloom per stem.

*Peduncle.*—Medium green, more or less suffused with reddish coloration. The length is approximately 4.5 cm. on average.

*Sepals.*—Upper surface: tomentose, greenish in coloration. Under surface: medium green, and the outer sepals have more or less appendiculate edges.

*Buds.*—Shape: oval. Length: approximately 3 cm. on average. Size: medium. Color upon opening: Upper surface: Tyrian Purple, Red-Purple Group 57A. Under surface: Rose Bengal, Red-Purple Group 57C.

*Flower.*—Shape: cup-like and semi-double. Diameter: approximately 12 cm. on average when fully open. Color (when opening begins): Upper surface: light Amaranth Pink, Red-Purple Group 68C. Under surface: light Amaranth Pink, Red-Purple Group 68C. Color (when blooming): Upper surface: light Amaranth Pink, Red-Purple Group 68C. Under surface: light Amaranth Pink, Red-Purple Group 68C. Color (at end of opening): Upper surface: light Amaranth Pink, Red-Purple Group 68B. Under surface: very light Amaranth Pink, Red-Purple Group 68C. Frangrance: strong. Lasting quality: long. Petal number: approximately 20 to 22 on average. Texture: very consistent. Petal drop: good. Stamen number: approximately 144 on average. Anthers: ochre, normal, located below the stigmas. Filaments: free standing, light fuchsia in coloration, of irregular heights. Pistils: approximately 84 on average. Stigmas: normal, yellowish in coloration. Styles: greenish, tomentose near the base, and sometimes bonded together. Receptacle: medium green, more or less stained with reddish coloration, smooth, in longitudinal section at the dehiscence of the anthers it is wide and in the shape of a pitcher.

Development:

*Vegetation.*—Very vigorous.

*Blooming.*—Abundant and continuous.

*Aptitude to bear fruits.*—Poor.

Resistance to frost.—Good.

*Resistance to diseases.*—Good.

I claim:

1. A new and distinct variety of Hybrid Tea rose plant characterized by the following combination of characteristics:

(a) forms in abundance on a continuous basis attractive long lasting semi-double pink blossoms which are Amaranth Pink on the upper surface and light Amaranth Pink on the under surface, (b) forms floral buds which exhibit an elegant exhibition-type configuration, (c) forms blossoms which are very fragrant, (d) forms very decorative vigorous vegetation, (e) exhibits á semi-erect growth habit, (f) is particularly suited for growing in parks and gardens, and (g) is not particularly affected by cryptogamic diseases;

substantially as herein shown and described.

* * * * *

MEIZELI